(12) United States Patent
Martorell

(10) Patent No.: US 12,161,417 B2
(45) Date of Patent: Dec. 10, 2024

(54) APPARATUS, SYSTEM, AND METHOD FOR DETERMINING INTRAOCULAR EYE PRESSURE

(71) Applicant: Click Therapeutics, Inc., New York, NY (US)

(72) Inventor: Anthony Martorell, New York, NY (US)

(73) Assignee: Click Therapeutics, Inc., New York, NY (US)

( * ) Notice: Subject to any disclaimer, the term of this patent is extended or adjusted under 35 U.S.C. 154(b) by 847 days.

(21) Appl. No.: 17/326,794

(22) Filed: May 21, 2021

(65) Prior Publication Data

US 2021/0361160 A1 Nov. 25, 2021

Related U.S. Application Data

(60) Provisional application No. 63/027,961, filed on May 21, 2020.

(51) Int. Cl.
| | |
|---|---|
| *A61B 3/16* | (2006.01) |
| *A61B 3/00* | (2006.01) |
| *G06T 7/00* | (2017.01) |
| *G06T 7/70* | (2017.01) |
| *G06T 7/80* | (2017.01) |

(52) U.S. Cl.
CPC .............. *A61B 3/16* (2013.01); *A61B 3/0025* (2013.01); *G06T 7/0012* (2013.01); *G06T 7/70* (2017.01); *G06T 7/80* (2017.01); *G06T 2207/10028* (2013.01); *G06T 2207/30041* (2013.01)

(58) Field of Classification Search
CPC ........... A61B 3/16; A61B 3/0025; A61B 3/14; A61B 3/165; G06T 7/0012; G06T 7/70; G06T 7/80; G06T 2207/10028; G06T 2207/30041; G06T 7/0016; G06T 7/593
See application file for complete search history.

(56) References Cited

U.S. PATENT DOCUMENTS 11,213,203 B2 * 1/2022 Mandel .................... A61B 3/16

* cited by examiner

*Primary Examiner* — James C. Jones
(74) *Attorney, Agent, or Firm* — Bochner PLLC; Andrew Bochner; Eric Kleinertz

(57) ABSTRACT

Provided is a system for measuring and assessing intraocular pressure (IOP). The system comprises a processor, a memory, a camera, and instructions written on the memory. The instructions when executed by the processor may cause the system to: capture an image of a user's eye; convert the image to a three-dimensional image; analyze the three-dimensional image; and calculate an IOP measurement.

24 Claims, 18 Drawing Sheets

```python
import numpy as np
import cv2
from math import sqrt, fabs
import bpy
import numpy as np def makeModel(DX, W):
    """
    Creating 3d model from coordinates and values which we received
    :param DX: list with coordinates
    :param W: eye width
    :return: void
    """
    for X in range(0, W-1, DX):
        for Y in range(0, H-1, DY):
            # Making faces of mesh
            face_v1= X+Y*W
            face_v2=X + 1 + Y* W
            face_v3=X + 1 + (Y+1) * W

Appending faces to faces list        faces.append((face_v1,face_v2,face_v3))

face_v1= X+Y*W
            face_v2=X  + (Y+1)* W
            face_v3=X + 1 + (Y+1) * W faces.append((face_v1,face_v2,face_v3))
```

Fig. 13 new_mesh=bpy.data.meshes.new("new_mesh")

Creating mesh with using verticles, edges and faces new_mesh.from_pydata(vertices,edges,faces)

Update mesh object new_mesh.update()

Make object from the mesh in .stl format new_object = bpy.data.objects.new("new_object",new_mesh)

view_layer=bpy.context.view_layer view_layer.active_layer_collection.collection.objects.link(new_object)

def takeSnap():
"""

Initialize camera and take snapshot

:return: void

"""

initialize the camera cam = cv2.VideoCapture(0)   # 0 -> index of camera s, img = cam.read()

if s: # frame captured without any errors cv2.namedWindow("cam-test", cv2.CV_WINDOW_AUTOSIZE)

cv2.imshow("cam-test",img)

cv2.waitKey(0)

cv2.destroyWindow("cam-test")

cv2.imwrite("face.jpg",img) #save image def getDimensions(coords):
"""

Fig. 13 (cont.)

```
Calculating coordinates
:param coords: list with coordinates
:return: object
"""
dimensions = {
   "a": coords[0].get("w") + coords[0].get("h"),
   "b": coords[0].get("y") / 2,
   "c": coords[0].get("y") / 2 + coords[0].get("x") / 2,
   "d": getZ(coords),
   "Y2": getY2(coords)
} return dimensions def checkEyeChangesBetweenDates(snap_1, snap_2):
    """
    Check eye changes between two photos with different dates
    :param snap_1: list with coordinates and fileinfo
    :param snap_2: list with coordinates and fileinfo
    :return: list
    """
        if snap_1.date != snap_2.date:
         if snap_1.get("x") != snap_2.get("x"):
                    print("Eye change positions")
                    return snap_2
        return snap_1
```

Fig. 13 (cont.)

```
def getZ(coords):
    """
    Difference in retinal position between corresponding image points
    :param coords: list with coordinates
    :return: float
    """
    p1 = pow(fabs(coords[1].get("x") - coords[0].get("x")), 2)
    p2 = pow(fabs(coords[1].get("y") - coords[0].get("y")), 2)
    T = fabs(sqrt(p1 + p2))
    d = fabs(coords[0].get("x") - coords[1].get("x"))
    return T / d def getY2(coords):
    """
    The geometric angle of change observed in the limbus region
    :param coords: list with coordinates
    :return: float
    """
    Dh = coords[0].get("w")
    Dv = coords[0].get("y")
    O = Dh / 2
    X = coords[0].get("x")
    Y = coords[0].get("y")

Y2 = pow((pow(Dh, 2) / 4) - pow((Dh / Dv), 2) * pow(X, 2), 2)

return Y2
```

Fig. 13 (cont.)

Loading face and eyes data cascades face_cascade = cv2.CascadeClassifier(cv2.data.haarcascades + 'haarcascade_frontalface_default.xml')

eye_cascade = cv2.CascadeClassifier(cv2.data.haarcascades + 'haarcascade_eye.xml')

Take snap from camera snap = takeSnap()

img = cv2.imread(snap)

gray = cv2.cvtColor(img, cv2.COLOR_BGR2GRAY)

faces = face_cascade.detectMultiScale(gray, 1.3, 5)

eyes_coord = []

Calculating base coords from eye and face snapshots for (x, y, w, h) in faces:

Creating image rectangle img = cv2.rectangle(img, (x, y), (x + w, y + h), (255, 0, 0), 2)

roi_gray = gray[y:y + h, x:x + w]

roi_color = img[y:y + h, x:x + w]

eyes = eye_cascade.detectMultiScale(roi_gray)

i = 0 for (ex, ey, ew, eh) in eyes:

if i == 2:

break

Append base eyes coordinates eyes_coord.append({

```
            "y": ey,
            "w": ew,
            "h": eh
        })
        # Creating image rectangle
        cv2.rectangle(roi_color, (ex, ey), (ex + ew, ey + eh), (0, 255, 0), 2)
        i += 1 print(eyes_coord)
Checking eye changes between 2 different photos
eyes_coord = checkEyeChangesBetweenDates(eyes_coord[0], eyes_coord[1])
# Getting coordinates (dimensions)
dimensions = getDimensions(eyes_coord)
print(dimensions)

# Showing image from camera in window
cv2.imshow('img', img)
cv2.waitKey(0)
cv2.destroyAllWindows()
# Creating model
makeModel(dimensions, eyes_coord[0].get("w"))
```

Fig. 13 (cont.)

DATABASE STRUCTURE

XML file example with OpenCV dataset

```xml
<opencv_storage>
<cascade type_id="opencv-cascade-classifier"><stageType>BOOST</stageType>
  <featureType>HAAR</featureType>
  <height>20</height>
  <width>20</width>
  <stageParams>
    <maxWeakCount>93</maxWeakCount></stageParams>
  <featureParams>
    <maxCatCount>0</maxCatCount></featureParams>
<stageNum>24</stageNum>
<stages>
    <_>
        <stageThreshold>-1.4562760591506958e+00</stageThreshold>
        <weakClassifiers>
            ......
        </weakClassifiers>
    </_>
</stages>
<features>
</features>
</opencv_storage>
```

Fig. 14

APPARATUS, SYSTEM, AND METHOD FOR DETERMINING INTRAOCULAR EYE PRESSURE

This application claims priority from U.S. Provisional Patent Application No. 63/027,961, filed on May 21, 2020, the contents of which are incorporated herein by reference.

FIELD OF THE INVENTION

Embodiments of the present invention relate generally to measurement of the fluid pressure inside the eye, called the intra-ocular pressure (IOP). More specifically, embodiments of the present invention relate generally to an apparatus and method for non-contact measurement of IOP changes using external surfaces angle measurements composed from three-dimensional imaging analysis. The apparatus and method may use imaging provided by smartphones and other devices that include or are directly or indirectly communicatively coupled to digital cameras.

BACKGROUND

The presence of elevated fluid pressure inside the eye, also known as IOP, is considered ocular hypertension when above a certain range. For most individuals, the normal range of IOP is between 10 mmHg and 21 mmHg. Thus, IOP above 21 mmHg is generally considered to be ocular hypertension.

Glaucoma is a group of eye diseases that result in damage to the optic nerve and cause vision loss. Types of glaucoma include primary open-angle glaucoma, angle-closure glaucoma, secondary glaucoma, and normal-tension or low-tension glaucoma. There are several risk factors for developing glaucoma including elevated IOP, age, ethnic background, family history of glaucoma, eye conditions, injuries, or surgeries, hyperopia, prolonged corticosteroid use, conditions that affect or are related to blood flow (such as migraines, diabetes, hypertension, and low blood pressure), high myopia, central corneal thickness of less than 0.5 millimeters, larger cup-to-disc ratio, and higher visual field pattern standard deviation.

As noted above, elevated IOP, generally one above 21 mmHg, is a risk factor for glaucoma, including primary open-angle glaucoma, among other diseases. Generally, the damage caused by glaucoma cannot be reversed so it is important to diagnose glaucoma as early as possible to begin treatment and stop damage to the eye. Treatment may include eye drops such as prostaglandins, beta blockers, alpha-adrenergic agonists, carbonic anhydrase inhibitors, rho kinase inhibitors, and miotic or cholinergic agents. Treatment may also include oral medications, such as a carbonic anhydrase inhibitor, as well as surgeries and other therapies, such as laser therapy, filtering surgery, drainage tubes, and minimally invasive glaucoma surgery.

Devices that measure intra-ocular pressure within the eye are generally known as tonometers. Tonometers specifically measure the amount of tension on the eye's outer wall (e.g., the cornea of the eye) through direct or indirect physical access (i.e., a puff of air) in order to deform, displace, or oscillate the membrane. IOP is then calculated using the pressure used to deform the outer eyewall. IOP measurements thus require special equipment, such as tonometers, requiring patients to be in a clinical setting for the measurement.

In general, there are two types of tonometers, differing by the mechanism of force used to measure IOP. The two types of tonometers include impression tonometers and application tonometers.

Impression tonometers apply a known pressure upon the wall of the cornea and measure the deformation produced on the wall of the cornea. Application tonometers apply a known deformation upon the wall of the cornea and measure the force required to produce the deformation.

Disadvantages of using tonometers include requiring a patient to physically access a clinic for IOP measurement, discomfort of the patient in having a tonometer in physical contact with his or her eye, requiring a medical professional to perform the measurement, and continuously having to measure IOP for chronic periods of time when managing conditions such as diabetes, glaucoma, high blood pressure, and the like.

Moreover, most patients do not see ophthalmologists or optometrists who are trained in and have access to tonometers, on a regular basis. Those that do may only see such clinicians once a year or even once every several years. However, IOP can sometimes increase quickly. For example, in acute angle-closure glaucoma (AACG), sudden severe IOP elevation can quickly damage the optic nerve.

It would be desirable, therefore, to provide apparatuses and methods for IOP measurement by a patient or a third party, who need not be a clinician, in a non-clinical setting without the use of specialized medical equipment such as tonometers. The patient or third party may then be able to monitor his or her IOP on a regular basis, at home. For example, the IOP may be monitored on a daily basis by a patient at home by using the camera(s) on a patient's smartphone.

SUMMARY OF THE INVENTION

The invention of the present disclosure may be a system, method, or apparatus for measuring and assessing intra-ocular pressure (IOP). In an embodiment, the system may comprise a processor, a memory, a camera, and instructions written on the memory, where the instructions when executed by the processor cause the system to capture one or more images of a user's eye, determine, for each of the one or more images, whether each of the one or more images were captured without error; convert each of the one or more images to one or more three-dimensional images, analyze the one or more three-dimensional images; and calculate an IOP measurement. The system may further include instructions that select a plurality of points on the user's eye and determine, for each of the plurality of points, a first camera origin coordinate and a second camera origin coordinate. In an embodiment, the system may also include instructions that determine, for each of the plurality of points, a first point projection and a second point projection, and determine, for each of the plurality of points, a camera distance, where the camera distance is distance between the first camera origin coordinate and the second camera origin coordinate.

In an embodiment, the system may also determine, for each of the plurality of points, a first retinal position and a second retinal position, and calculate, for each of the plurality of points, a difference in retinal position, where the difference in retinal position is equal to the difference between the first retinal position and the second retinal position. The system may include instructions that further calculate, for each of the plurality of points, a depth value, where the depth value is a function of the first camera origin coordinate, the second camera origin coordinate, the first point projection, and the second point projection, and where the depth value is proportional to a quotient of the camera distance and the difference in retinal position. The system may then create the one or more three-dimensional images based on the depth value for each of the plurality of points on the user's eye.

In an embodiment, the instruction to calculate the IOP measurement when executed by the processor further causes the system to determine, for each of the one or more three-dimensional images and/or one or more images, a horizontal corneal diameter ($D_H$), a vertical corneal diameter ($D_V$), and a geometrical center of the corneal projection (O). The instructions may then cause the processor to determine, for each of the one or more three-dimensional images and/or each of the one or more images, X and Y based on a first camera origin coordinate and a second camera origin coordinate; and calculate $Y^2$ via:

$$Y^2 = \frac{D_H^2}{4} - \left(\frac{D_H}{D_V}\right)^2 \cdot X^2$$

where $Y^2$ may be proportional to the eccentricity of the cornea and the IOP measurement may be a function of $Y^2$. The system may further determine an angle at a limbus region of the user's eye based on the depth values for each of the plurality points on the user's eye, where the angle at the limbus region is proportional to the IOP measurement.

In an embodiment, the instructions when executed by the processor may cause the system to calibrate the camera. The calibration may include an eye zone, where an eye zone is presented to the user during calibration of the camera. The instructions when executed by the processor may cause the system to transmit an alert to the user if the calibration is unsuccessful. The system may also instruct the user to place the camera a pre-determined distance from the user's eye and to instruct the user to place the user's eye within the eye zone. In an embodiment, the one or more images are configured to capture the user's cornea, limbus, and sclera.

In an embodiment, the instructions when executed by the processor may cause the system to capture one or more subsequent images of the user's eye, determine whether the one or more subsequent images were captured without error, convert each of the one or more subsequent images to one or more three-dimensional subsequent images, analyze the one or more subsequent three-dimensional images, and calculate a subsequent IOP measurement. In an embodiment, the system may include instructions to compare the IOP measurement and the subsequent IOP measurement, where the IOP measurement may be a baseline IOP. In an embodiment, the instructions when executed by the processor may cause the system to alert the user if the subsequent IOP measurement differs from the baseline IOP by a pre-determined variance.

In an embodiment, the system may the system determine whether the one or more images and the one or more subsequent images were captured on a same date and prepare a first list of coordinates and a second list of coordinates, where the first list of coordinates contain coordinates of the user's eye as represented in the one or more images and the second list of coordinates contain coordinates of the user's eye as represented in the one or more subsequent images. The first list of coordinates and the second list of coordinates may be referred to as "snap_1" and "snap_2." The system may also determine whether the first list of coordinates and the second list of coordinates contain the same coordinates and return the second list of coordinates if the first list of coordinates and the second list of coordinates are unequal.

BRIEF DESCRIPTION OF THE DRAWINGS

FIG. 13 is an example of code that may be utilized for algorithms.

FIG. 14 is an example of code that may be utilized to structure a database.

DETAILED DESCRIPTION

Figure 1:
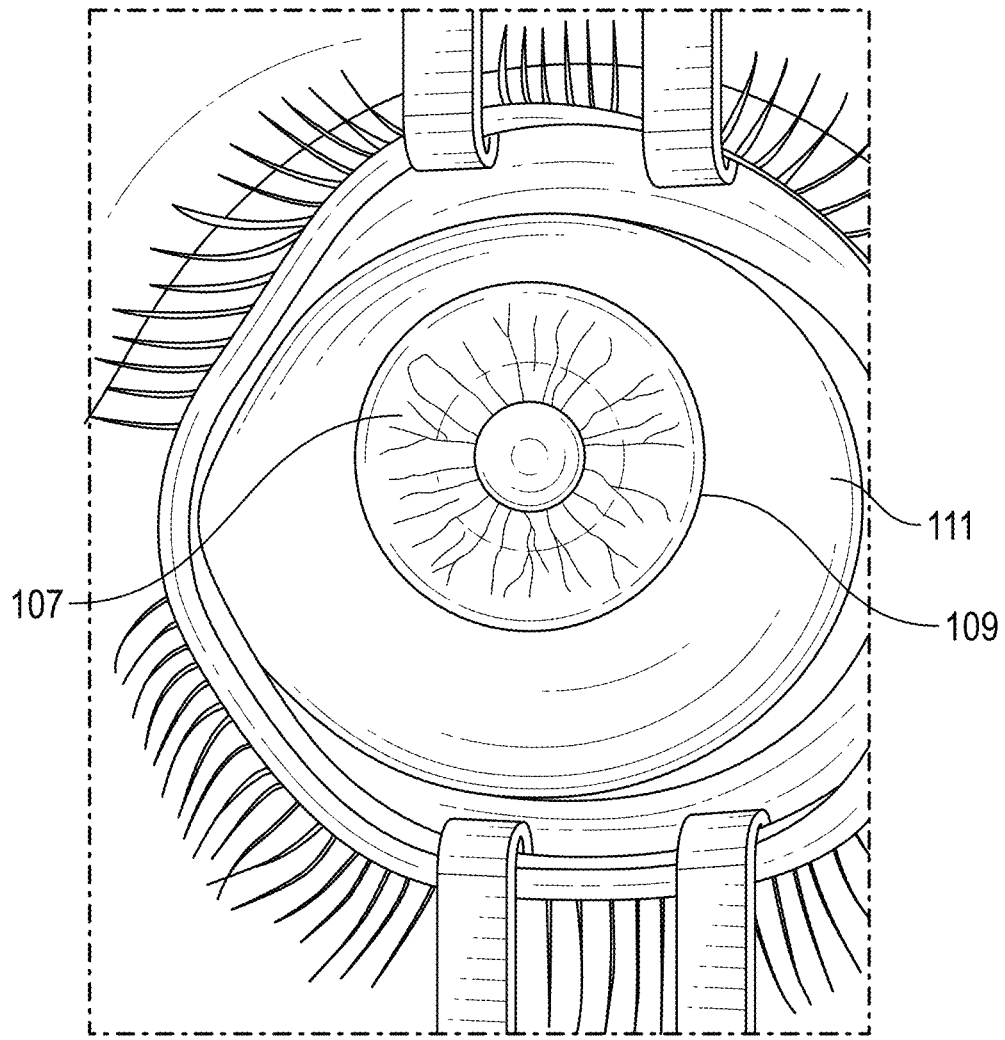
FIG. 1 is a front view of an eye demonstrating the major relevant anatomy.

Disclosed herein are systems, apparatuses, and methods for non-contact measurement of IOP. The problems outlined above are in large part solved by the apparatuses and methods of embodiments of the present invention.

In particular, embodiments of the invention are non-invasive to the eye and do not affect IOP, nor disturb the eye surface in any way. An IOP measurement may incorporate strain displacement relationships (for example, the continuum of the eye), equilibrium conditions (for example, fluid pressures or membrane stresses), or boundary conditions (for example, ambient and physiological conditions).

The eye naturally satisfies all four of these conditions. The eye is comprised of fluid filled dual membranes (the Cornea and Sclera), is of a spherical-like shape, is joined at the limbus by a fibrous ring that acts to react to the forces of the ciliary muscles in changing the shape of the elastic lens to focus an image on the retina. The external contour of the eye is the result of the shape, size, and elasticity of the membranes and the differential pressure (IOP) between the inside of the eye relative to that of the pressure outside of the eye.

The aqueous humor in the anterior chamber directly behind the corneal membrane is a part of the eyes focusing apparatus and fundamental source of IOP. Aqueous humor is generated via the ciliary body and performs several functions for the eye, including nutrition for ocular tissues, and a refractory index. Aqueous humor is produced in the posterior chamber of the eye and drained to the anterior chamber. It is then ported out from the anterior chamber through the trabecular meshwork and into blood vessels. IOP is a result of the equilibrium of fluid pressure between aqueous and vitreous humor and the external atmospheric pressure. The external contour of the cornea and Sclera, at their junction, called the limbus, is determined by the difference between internal and ambient pressure (IOP), the stresses and strains within the corneal and scleral membranes, and the stresses and strains in the fibrous reinforcement at the limbus. In glaucoma, aqueous humor cannot appropriately strain into the vitreous humor, causing an increase in IOP, and change in geometric angle of the eye/limbus.

While tonometers rely on the physical deformation of the eyewall for IOP measurement, embodiments of the present invention provide a non-invasive, repeatable, and digital therapeutic capability for IOP measurement using a user's smartphone or other device that includes or is communicatively coupled to a digital camera.

Smartphones are generally phones that are capable of performing many tasks such as making and receiving calls, connecting to the Internet, receiving and sending email, taking photographs or video, browsing the web, downloading and running apps, storing data, sending and receiving data, and the like.

Smartphones generally include a processor for controlling the smartphone, a hard drive to store the operating systems, apps, and user created and/or downloaded data/content, temporary memory such as RAM or ROM, a cellular chip to communicate with a base station, a WiFi chip to communicate with a wireless access point, a screen to display information to the user (which may be a touchscreen and may receive input from the user) and one or more sensors, described in more detail below.

Smartphones may include multiple sensors and hardware including a cellular chip, a WiFi chip, a microphone, a speaker, a magnetometer, a GPS, a barometer, a gyroscope, an accelerometer, a proximity sensor, an ambient light sensor, a vibration sensor, an orientation sensor, touchscreen sensors, fingerprint sensors, a pedometer, barcode/QR code sensors, a heart rate sensor, a thermometer, an air humidity sensor, a Geiger counter, as well as one or more cameras. The cameras may include one or more forward-facing cameras and one or more rear-facing camera. The cameras may be capable of taking still images, as well as video. The images and/or video captured by the camera may be stored on the hard drive of the smartphone and/or transmitted to a server communicatively coupled to the smartphone.

As noted above, embodiments of the present inventions relate to using digital images of the eye captured by a digital camera on, for example, a smartphone, to determine IOP. Specifically, embodiments of the present invention involve the image capture of the surface of the eye using a digital camera (for example, of a smartphone of the user), where a two-dimensional (2D) image is converted to a three-dimensional representation of the eye surface. In particular, embodiments of the present invention determine IOP by non-invasive methods via measuring the geometry of the eye surface to changes in pressure.

FIG. 1 illustrates a frontal view of a human eye, where the cornea 107, limbus region 109, and sclera 111 regions are identified.

Figure 2:
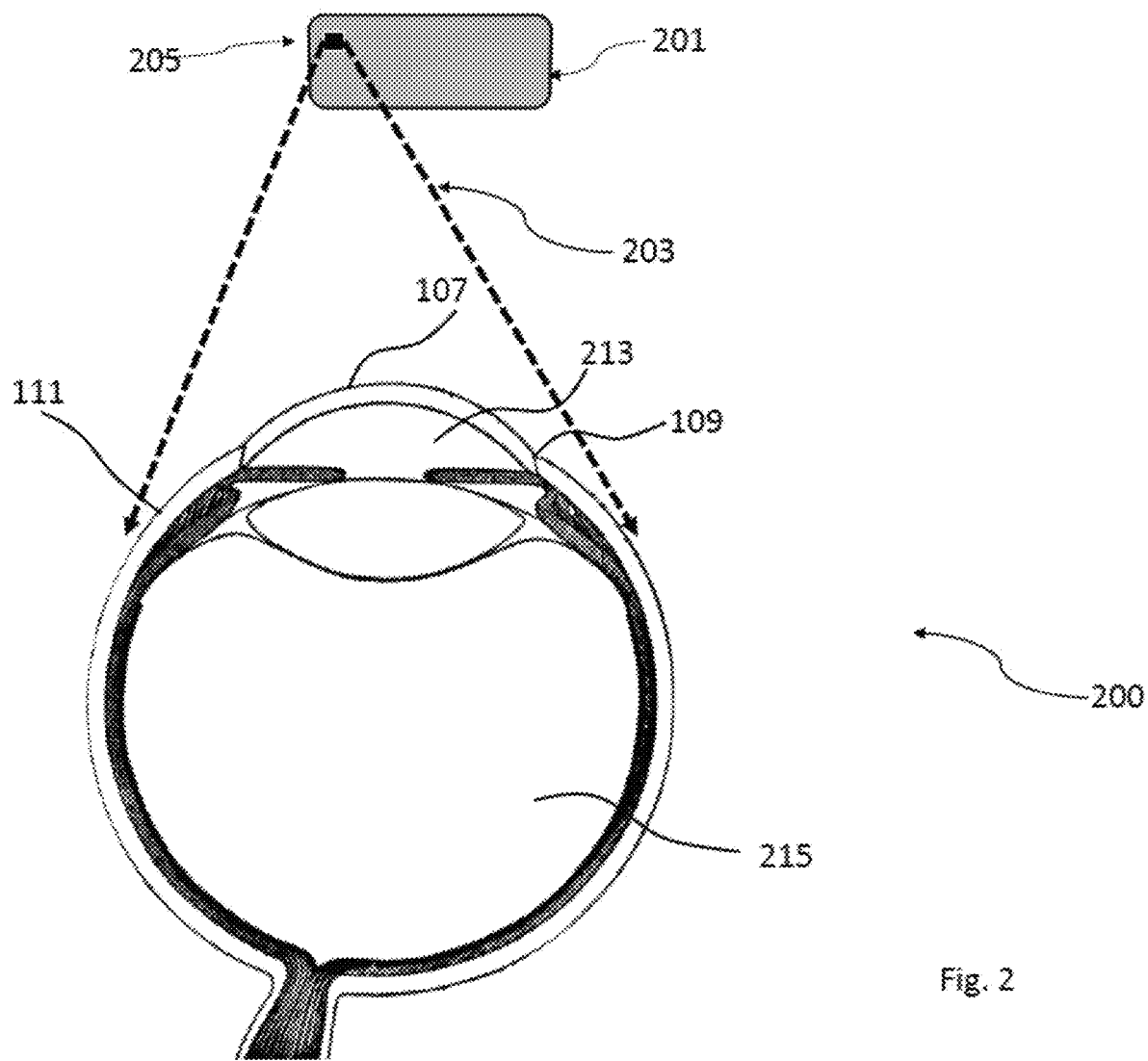
FIG. 2 is a cross-sectional view of an eye arranged in optical communication with a smartphone camera and thus its imaging software component, further arranged to capture the cornea/sclera/limbus region for IOP calculation/determination.

FIG. 2 shows a cross-sectional view/illustration of a human eye 200. A smart phone device 201 may capture an image (or series of images) 203 of the eye through its camera 205. In an embodiment, the image captures the view of the surface of the cornea 107, limbus region 109, and sclera 111. In the anterior chamber underneath the cornea is aqueous humor 213, opposite from the posterior chamber containing vitreous humor 215. Changes in (aqueous and vitreous) humor volume 213 and 215 are causes for changes in eye IOP.

Figure 3:
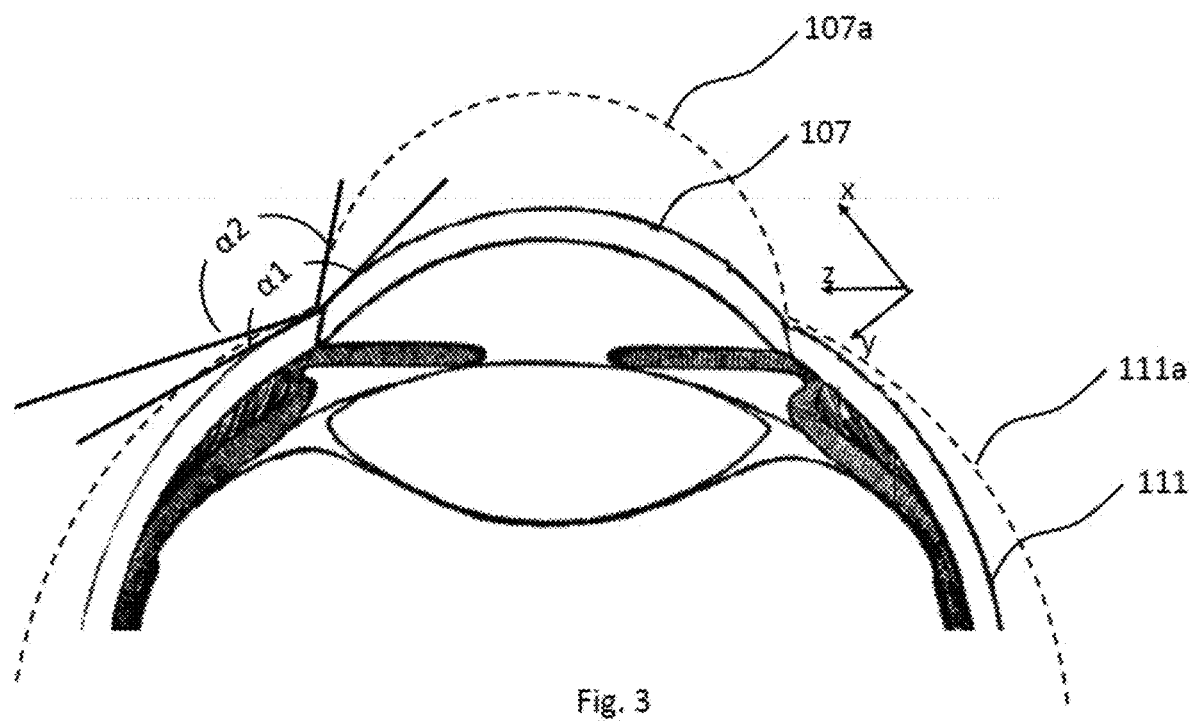
FIG. 3 is a cross-sectional view of the eye showing the limbus region's cornea-sclera angle annotation for IOP measurement.

FIG. 3 shows a cross-sectional view/illustration of the anterior portion of the human eye at two separate IOPs. 107 and 111 demonstrate the cornea and sclera, respectively, where the sclera-cornea angle ($\alpha 1$) is measured for a baseline IOP calculation. 107a and 111a demonstrate changes in the cornea and sclera angle, respectively, following a change in IOP measured by ($\alpha 2$).

Measurement of the IOP by non-invasive means may be accomplished by the user taking multiple digital images of his or her eye using the digital camera in his or her smartphone. Smartphones that have more than one camera facing one side may be used to capture an image from more than one camera on the same side at the same time. In alternate embodiments, the digital camera may be that of a laptop, desktop computer, or other device.

Figure 4:
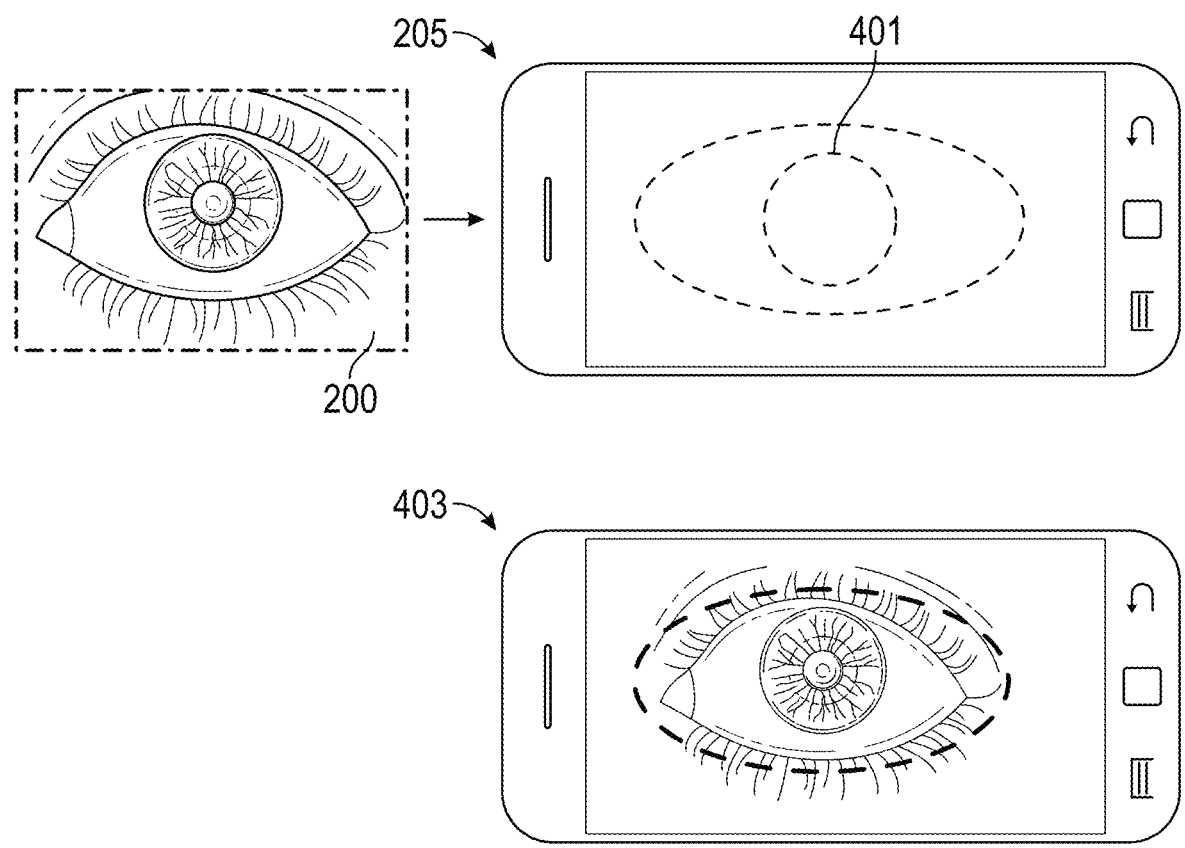
FIG. 4 is a flowgraph showing eye calibration using a smartphone.

FIG. 4 illustrates the process of eye calibration for IOP measurement, where the user would place their smartphone camera 205 a distance away from their eye 200 and aim to fit their iris in the zone marked 401. The user's eye should overlap with the camera's eye's zones, as shown in 403. Another embodiment of the invention is the capability of a voice guide running on the smartphone that helps the patients during the process of taking images of their eye of FIG. 4. This process may include making sure the camera is angled correctly, the camera is at the correct distance from the eye, the eye is open in a correct manner (e.g., not partially closed, so as to obscure a portion of the cornea, sclera, limbus region, or other parts of the eye, the camera flash is on or off, holding the eye open until the images are taken, and/or how/when to take the picture, and read/interpret IOP results). As a non-limiting example, if the camera is too far from the eye such that the iris is not in zone 401 or too close such that the iris is not in zone 401, a voice and/or message would indicate to the user to move the camera closer or further to the eye, respectively.

Figure 5:
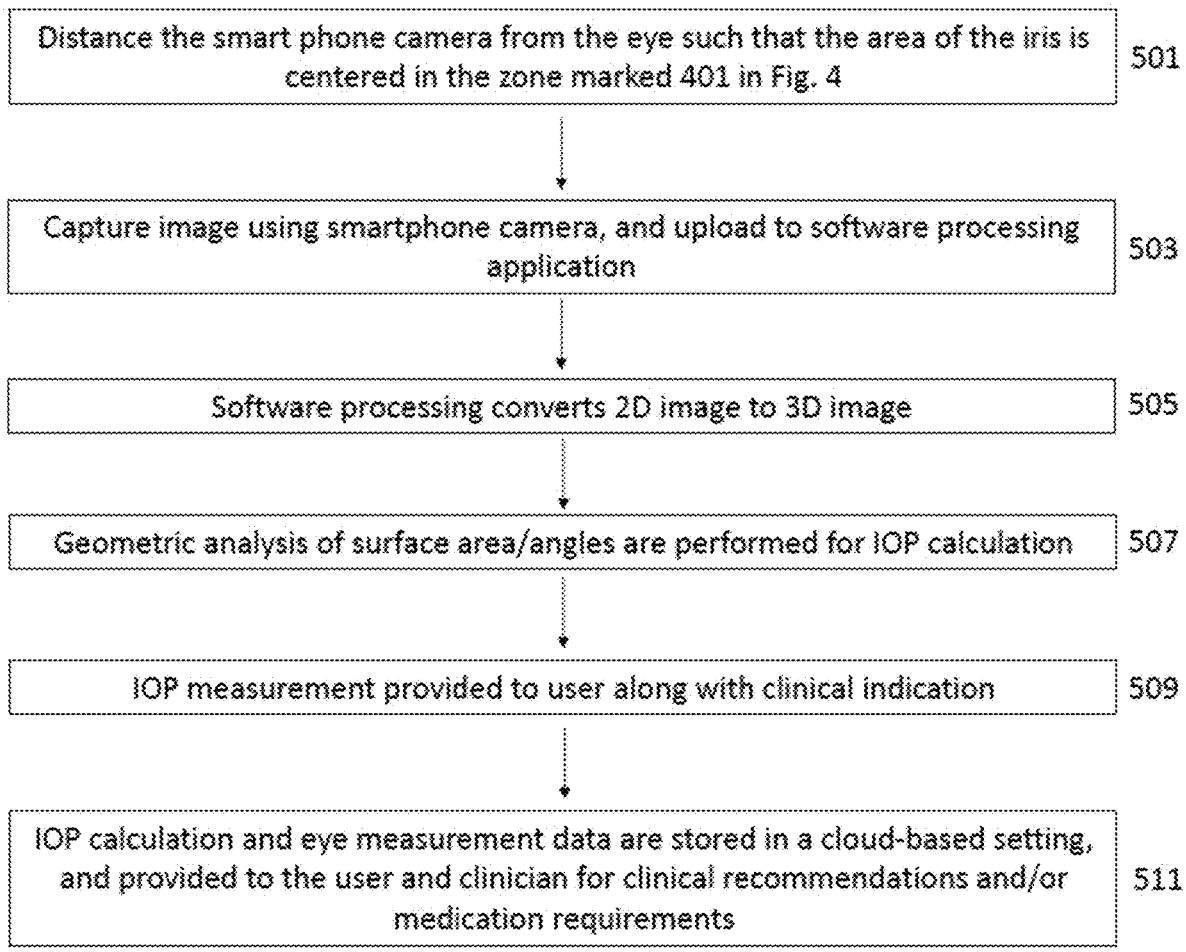
FIG. 5 is a flowchart indicating the procedure for image calibration, image dimension conversion, geometry analysis and IOP measurement, data storage, and alerting the user/clinician regarding IOP measurement(s) and medication adherence.

FIG. 5 shows a flowchart describing the process from eye calibration to data storage. In step 501 of FIG. 5, the app running on a user's smartphone asks the user to distance the smartphone camera from the eye such that the area of the iris is centered in the zone marked 401 in FIG. 4. In step 501, the app may determine whether the user has correctly positioned the smartphone such that the iris is centered in zone 401, chance the distance between the smartphone and the eye, ask the user to turn the flash on or off, control the flash automatically, and the like.

In step 503 of FIG. 5, an image is captured using a smartphone camera. The image may be captured manually by the user in response to a request from the app (by a text-based message or a voice message to capture the image) or may be automatically captured once the app determines that the iris is centered in zone 401 of FIG. 4. Once the image is captured, it may then be available to the app and/or software running on a server communicatively coupled to the smartphone for processing.

In step 505 of FIG. 5, the app converts a 2D image to a 3D image as discussed in more detail below and, in step 507, the app performs geometric analysis of surface area/angles for the IOP calculation, as also discussed in more detail below.

Measurement of the IOP may be accomplished by measuring changes in surface-to-height (i.e. in relation to the height distance from the apex of the cornea to the surface or the base of the sclera), area (measuring the surface of the cornea and sclera in cm$^2$), convexity (curvature of the eye exterior), or the angle of change in the limbus region (produced from the junction between the sclera and cornea, where a horizontal line at the sclera produces the x-axis, and a vertical line at the cornea junction produces the y-axis). The areas of the cornea and sclera are used for determining IOP by providing the potential change in size of the eye; increased area may indicate increased IOP. Convexity is another iteration of measuring changes in the surface of the eye, whereas a more acutely angled cornea may indicate increased IOP. Such determinations are possible because as IOP fluctuates, the sclera and cornea expand and contract relatively independently, causing measurable changes in height, area, convexity, and the angle between the sclera and cornea (limbus). Such angular changes can be measured from 3D geometry analysis of the eye surface. In general, eye surface measurements occur from geometric analysis of 3D representational figures.

Short-term changes in the sclera-corneal angle may be quickly measured and interpreted using embodiments of the present invention. This allows for an improved method of IOP measurement, recommended for the appropriate treatment of various medical conditions (e.g., glaucoma). In an embodiment, geometric measurements made from physical changes to the eye contour, specifically the limbus region, may be compared with the previously stored baseline IOP information; changes in the sclera-cornea angle would be converted to changes in IOP. For each patient, a unique eye-surface measurement calibration may be stored, allowing for determination of their specific baseline IOP measurement. Baseline IOP may be determined at a stable pressure at which it is not pathological (not high). Thus, any pathological variation from this pressure may alert the system. Baseline calibration may be determined at a period when the user is confident that eye IOP is normal (for example, this could be following the application of eye medication, doctors visit, or another device).

Embodiments of the present invention allow for the non-invasive determination of IOP and are readily adapted for home or ambulatory monitoring of glaucoma patients, or other patients with pathological variances in IOP. Data for IOP may be measured from geometric analysis of sclera-cornea angle changes, as it compares to the baseline IOP data stored on the smartphone or a server communicatively coupled to the smartphone (e.g., a server at the physician's office).

In an embodiment, repeatable IOP measurements can be obtained in practice by placing the smartphone in front of the eye, in which the camera will automatically adjust its focus to the eye-surface contour, and take an appropriate flash or non-flash image. The 2D image may then be converted to a 3D representation of the eye surface, allowing for the calculation of geometric measurements and angles in step 507 of FIG. 5. In an embodiment, this data may be stored in the patient's mobile device or smartphone in order for measurements to be easily accessible, and allow patients to know appropriate trends, changes, and potentially pathological increases in IOP.

2D to 3D image conversion and surface angle calculations may be performed through an application-based software algorithm tool running on a smartphone device or a server communicatively coupled to the smartphone. In an embodiment, the algorithm utilizes information captured from a set of images from different viewpoints of the same scene (i.e. the right eye). Following image capture, a set of corresponding points in the image pair may be determined. In an embodiment, using a triangulation method, the depth information of the image(s) is retrieved and then compared to baseline depth measurements for IOP calculation. Depth information from the images may use various points of the eye to create a 2D-to-3D surface (these measurements may be helpful in understanding the surface-to-height data for IOP measurement). Geometric angle changes at the limbus may also be calculated using changes in depth at the cornea and sclera. Changes in depth may be calculated using the diagram illustrated in FIG. 15A.

Figure 15A:
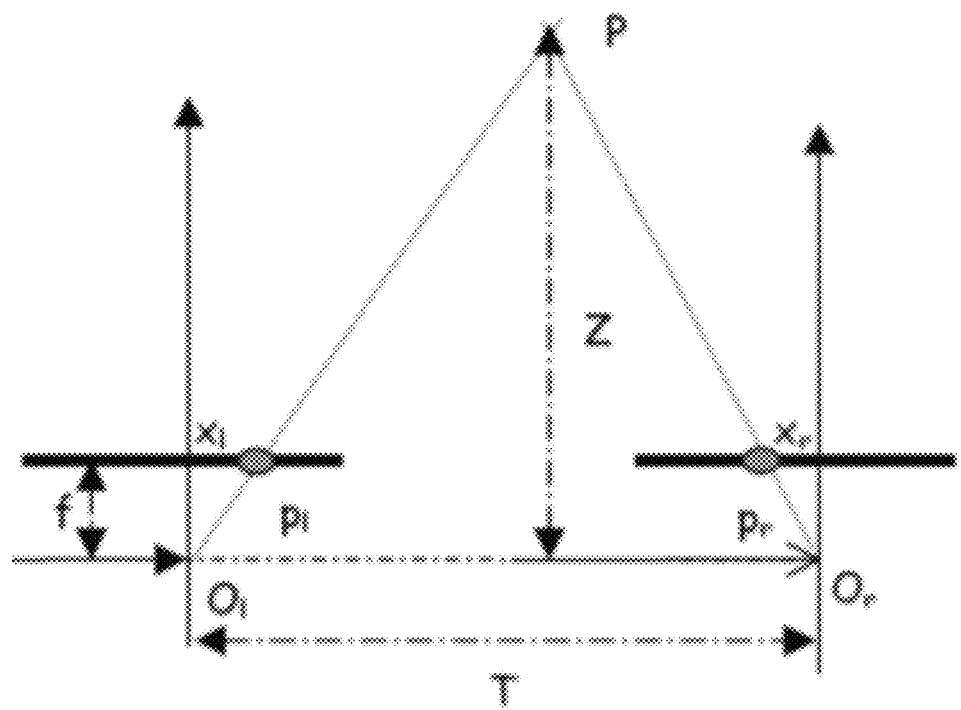
FIGS. 15A-15B are illustrations of geometric angle changes at the limbus.

Referring to FIG. 15A, in an embodiment, $P_l$ and $P_r$ are the projections of the 3D point P on the left image and right image; P can be any part of the eye that is to be converted from 2D to 3D. $O_l$ and $O_r$ are the origin of camera coordinate systems of the left and right cameras. T is the distance between the camera coordinates. Based on the relationship between these projections (P, $P_l$ and $P_r$) and (P, $O_l$ and $O_r$), the depth value Z of the point P can be obtained:

$$Z = f\frac{T}{d}$$

In the aforementioned expression, $d=x_r-x_l$ may measure the difference in retinal position between corresponding image points. In an embodiment, f may be the distance between a camera and the projection of a point. The disparity value of a point is often interpreted as the inversed distances to the observed objects. The geometric angle of change observed in the limbus region is calculated using depth information from corresponding points of the image, specifically the cornea and sclera. This measurement can be characterized by the diagram illustrated in FIG. 15B.

Figure 15B:
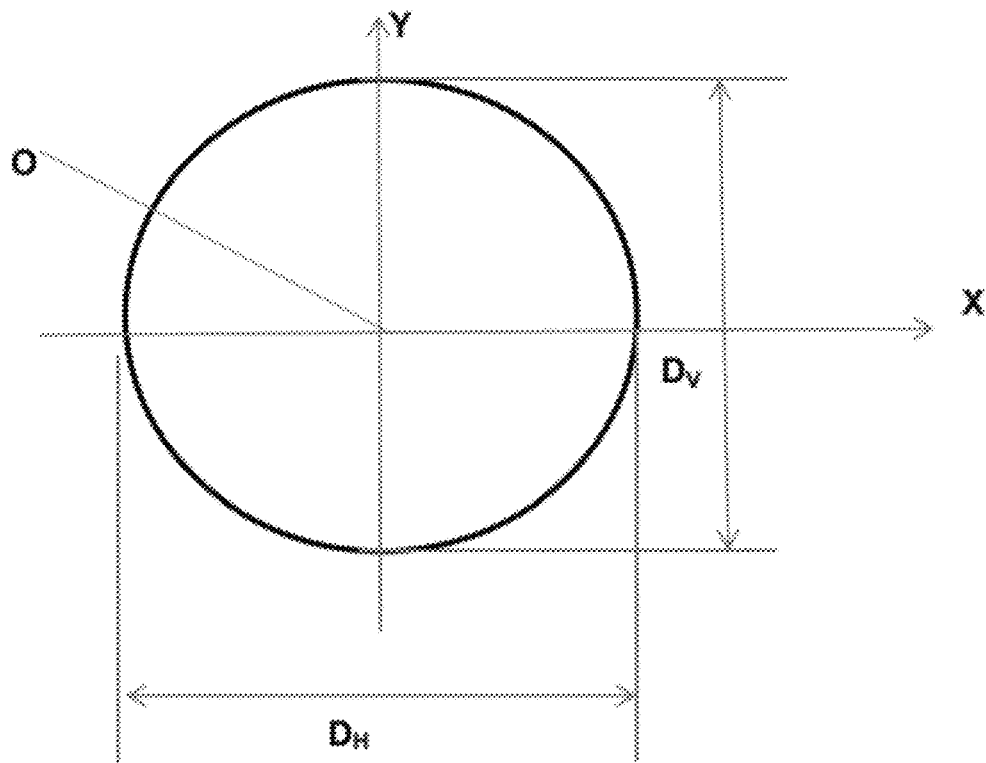

Referring to FIG. 15B, in an embodiment, $D_H$=horizontal corneal diameter; $D_V$=vertical corneal diameter; O=geometrical center of the corneal projection; and X and Y are coordinate components (for example, horizontally and vertically representing a point along the corneal circumference on a 2D plane) from the camera coordinate systems. X and Y may be coordinates as seen from the point of view of one or more cameras. X and Y may be points on the circumference of the cornea, utilized by the system for determining measurements along the eye (for example, corneal diameters or general corneal shape).

A difference between $D_H$ and $D_V$ may indicate that the limbus is an ellipse, with an equation that can be determined via the following equation:

$$Y^2 = \frac{D_H^2}{4} - \left(\frac{D_H}{D_V}\right)^2 \cdot X^2$$

In an embodiment, the eccentricity of an ellipse or any other ellipse characteristic may be used as a metric to measure IOP. In such an embodiment, the aforementioned $Y^2$ measurement may be used as measure for the eccentricity of the cornea. In one embodiment, the elliptical nature of the cornea may be calculated in 2D (for example, by analyzing the cornea as it appears in the 2D photographs). However, in another embodiment, the elliptical nature of the cornea may be analyzed in 3D (for example, by analyzing the 3D rendering of the eye).

In a further embodiment, the eccentricity of the cornea may be analyzed via the aforementioned $Y^2$ expression, where the eccentricity of the cornea is utilized as a factor in determining other characteristics of the eye. In such an embodiment, the eccentricity of the cornea may be utilized to determine the size of the cornea, which may be a factor in measuring the angle between the sclera and cornea.

In an embodiment, a 3D equation may be fashioned to determine the volume of the cornea (or other component of the eye). As a non-limiting example, the corneal volume may be calculated by utilizing the circumference as measured via the ellipse expression and the height of the cornea as measure via the aforementioned depth expression. In another embodiment, the volume of the cornea may be calculated by combining the corneal ellipse measurement with the angle as measured at the cornea-sclera border. The volume of the cornea may be directly related and/or proportional to the IOP.

In an embodiment, the IOP may be calculated foregoing the depth measurement. In such an embodiment, a change in the angle at the cornea-sclera border may correspond to a determinable change in surface elevation. Such an assumed change in surface elevation may reflect a change in IOP. As a non-limiting example, utilizing the aforementioned method of IOP determination may be favorable when there is a sizeable quantity of organic material disposed on or in the cornea. In such a non-limiting example, the organic material may prevent the measured depth from changing drastically under even high IOP conditions.

In sum, the patient may take the eye images using a smartphone device with a camera, the images may then be automatically uploaded/transferred to the smartphone application software, which is then converted to a 3D surface; application-based software may then calculate eye surface angles for IOP measurement and the appropriate clinical indication. In step 509 of FIG. 5, this information is transmitted, downloaded, or uploaded to the physician or other clinician for ease of use. In step 511 of FIG. 5, the IOP calculation and eye measurement data are stored in a cloud-based setting (or on the smartphone), and provided to the user and clinician for clinical recommendations and/or medical requirements (such as prescribing eyedrops).

In an embodiment, divergence may be detected based on changes in the corneal diameter (for example, the horizontal or vertical corneal diameters) and/or angles of the limbus. In an embodiment, the IOP measurement is not directly calculated in terms of pressure. In such an embodiment, the IOP measurement may be a function of the various ocular characteristics that vary dependent on IOP. As a non-limiting example, the system may recognize that an individual with a drastic increase in limbus angle has an IOP of a certain comparative degree, without determining the exact pressure on the eye. In a further embodiment, an IOP measurement is directly related to and may be a function of the value of $Y^2$. In alternative embodiments, an IOP measurement relationship may be drawn from various characteristics of the eye (for example, limbus angle, pupil height, etc.). In an embodiment, the system may assign a unitless value to IOP (for example, an IOP scale ranging from 0.0 to 10.0, where the unitless value is related to observable ocular characteristics).

Embodiments of the present invention may analyze 2D renderings of the eye to determine IOP or other characteristics of the eye. In an embodiment, the 2D renderings and subsequent 2D-related measurements may be used to analyze or map 3D renderings of the eye. In a further embodiment, 2D-derived measurements may be used in combination with 3D-derived measurements to determine IOP (for example, an IOP measurement rooted in both the depth of the cornea as derived from the 3D rendering and the corneal eccentricity as derived from a 2D analysis of the cornea).

Embodiments of the present invention may also advise/instruct patients when there are changes in IOP during normal physiological activity (i.e. body position change, exercise) and/or the external environment (atmospheric pressure or temperature changes), which may not be considered pathological and/or a concern. This may be performed through the use of external hardware devices, such as Apple watches, which monitor heart rate and blood pressure. For example, if a user is performing physical exercise and checks IOP, the application will consider his physiological activity to inform normal and abnormal IOP. If IOP is high during exercise, it may be because of momentary increased blood pressure; thus the application may advise the user to re-check IOP following exercise, or potentially modify exercise if IOP is dangerously high. However, changes in IOP that occur outside of normal physiological or environmental occurrences may warn the patient (through the smartphone, such as through a message, alert, ring, noise, and the like) suggesting that treatment, such as eyedrops, be administered for injury prevention (i.e. retinal nerve injury in glaucoma).

In an embodiment, the invention of the present disclosure includes an eye-image capture algorithm. In an embodiment, this algorithm may be configured to emit a sound that increases in intensity as the camera's view of the eye aligns more closely with a template/frame. (for example, with "beeping" signals to assist the user in capturing the best alignment). A user may capture two photographs per date, one to the left and the other to the right of the cornea. The left and right photographs may be referred to as the first and second images.

In an embodiment, the invention of the present disclosure includes an eye modeling algorithm. In an embodiment, this algorithm may be configured to determine measurements of the height distance from the apex of the cornea to the surface or the base of the sclera, the area of the cornea, the convexity of the cornea, and/or the angle between the cornea and the sclera.

In an embodiment, the invention of the present disclosure includes an eye divergence and change algorithm. In an embodiment, this algorithm may be configured to report a warning if any measurements are abnormal based on pre-set measurement ratio thresholds or if measurement changes exceed a pre-set percentile between any first and second dates, where the pre-set percentile takes the time distance between the first and second dates into account.

An embodiment of the invention of the present disclosure includes an agorithm, or set of algorithms, for creating a 3D model of the eye based on a set of two photographs obtained from a smart phone, determine whether the eye is abnormal based on the eye dimensions, or whether the dimensions of the eye are changing too quickly over time.

Any of the aforementioned algorithms may be stored on the hard drive and executed by the processor.

Figure 6:
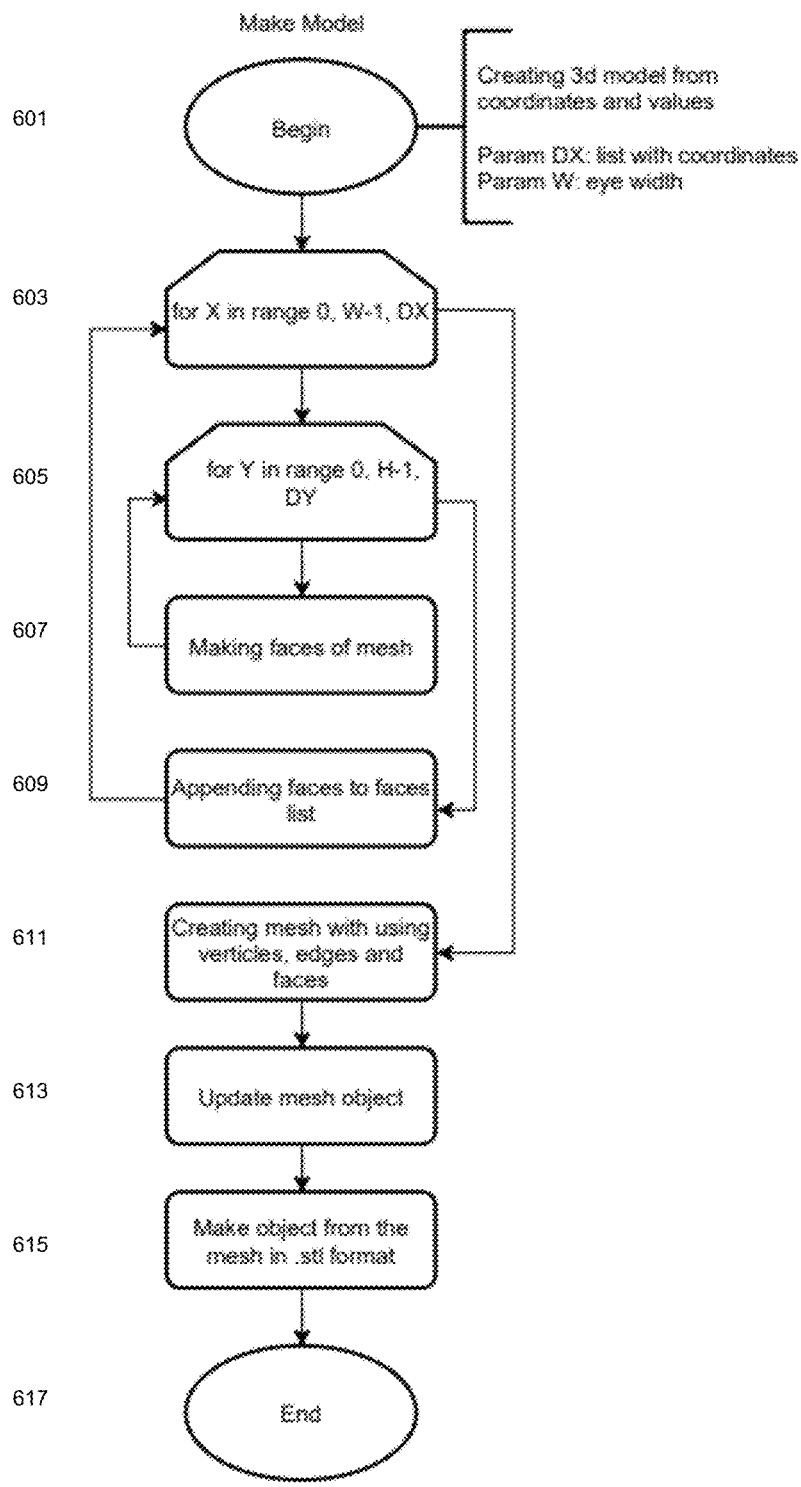
FIG. 6 is a flowchart describing the procedure for 3D model creation.

FIG. 6 shows a flowchart describing the process of an algorithm configured to create a 3D model from coordinates and values that are received from a list with coordinates (param DX), where the coordinates may include eye width (param W). In step 601 of FIG. 6, the algorithm may begin (for example, by beginning execution on the computer, device, or processor). In step 603, the algorithm may take into account data for X in range 0, W−1, DX, and in step 605, for Y in range 0, H−1, DY. In step 607, the algorithm may then make faces of mesh and may once again do so for Y in range 0, H−1, DY. In an embodiment, the faces of mesh may be a surface defined by a number of vertices (for example, an ordered list configured to track the vertices of points on the eye). In step 609, the algorithm may be configured to append faces to a face list for X in range 0, W−1, DX. Next, in step 611, the algorithm may create mesh by using vertices, edges, and faces. At this point, the algorithm may continue to step 613 where the mesh object may be updated. In step 615, an object may be made from the mesh (for example, in a .stl format). In step 617, the algorithm may end.

Figure 7:
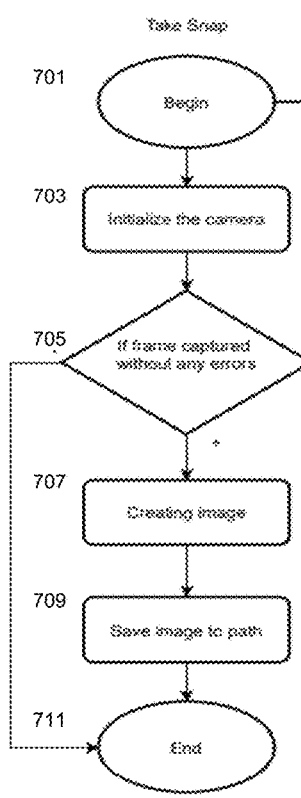
FIG. 7 is a flowchart describing the procedure for initializing a camera and taking snapshots.

FIG. 7 shows a flowchart describing the process of an algorithm configured to initialize a camera and take a snapshot. In step 701, the process to initialize a camera and take a snapshot may begin. In step 703, the apparatus may initialize the camera. In step 705, the apparatus determines if the frame has been captured without any error. If the frame has been captured without error, then in step 707 and step 709, the apparatus creates the image and saves the image to a path, respectively. Next, in step 711, the algorithm may end. If the frame has been captured with errors, then process may continue to step 711, ending the algorithm.

Figure 8:
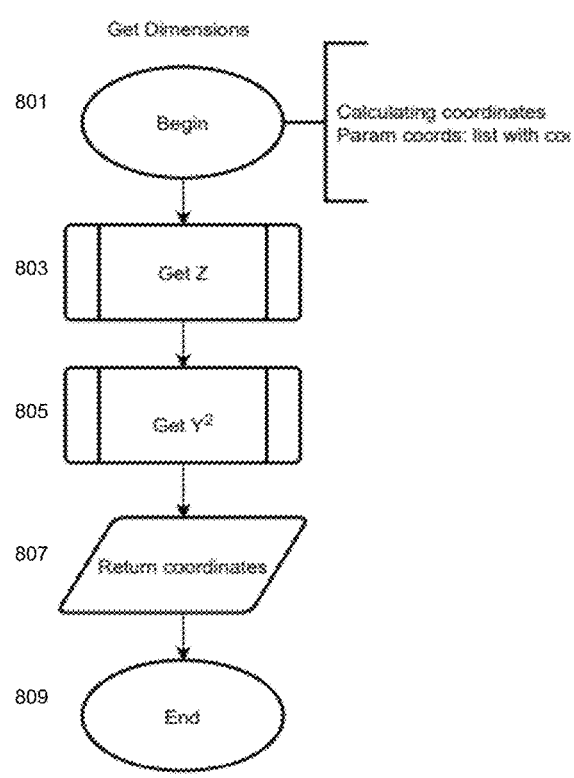
FIG. 8 is a flowchart describing the procedure for calculating coordinates.

FIG. 8 shows a flowchart describing the process of an algorithm configured to calculate coordinates (for example, from a list with coordinates). In step 801, this algorithm may begin. In step 803, the algorithm may get Z. For example, the system may define a function for getting Z that determines the difference in retinal position between corresponding image points. In step 805, the algorithm may get $Y^2$. For example, the system may define a function for getting $Y^2$ that determines the geometric angle of change observed in the limbus region. In step 807, the algorithm may return the calculated coordinates and, in step 809, the algorithm may end.

Figure 9:
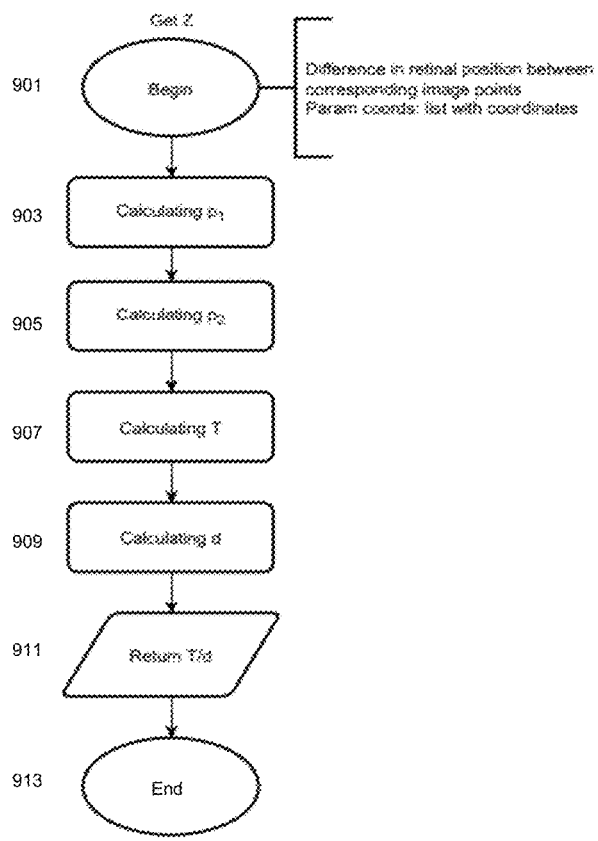
FIG. 9 is a flowchart describing the procedure for determining the difference in retinal position between corresponding image points.

FIG. 9 shows a flowchart describing the process of an algorithm configured to determine the difference in retinal position between corresponding image points. In step 901, this algorithm may begin. In step 903, the algorithm may calculate $P_1$. $P_1$ may be determined with the following expression: pow(fabs(coords[1].get("x")−coords[0].get("x")), 2). In an alternate embodiment, $P_1$ may be determined with any similar expression. In step 905, the algorithm may calculate $P_2$. $P_2$ may be determined with the following expression: pow(fabs(coords[1].get("y")−coords[0].get("y")), 2). In an alternate embodiment, $P_2$ may be determined with any similar expression. $P_1$ and $P_2$ may be image points used to further determine the retinal positional difference. In step 907, the algorithm may calculate T. T may be determined with the following expression: fabs(sqrt(p1+p2)). In an alternate embodiment, T may be determined with any similar expression. In step 909, the algorithm may calculate d, which may be determined with the expression: fabs(coords[0].get("x")−coords[1].get("x")). However, in an alternate embodiment, d may be determined with any similar expression. In step 911, the algorithm may return T/d. Finally, in step 913, the algorithm may end.

Figure 10:
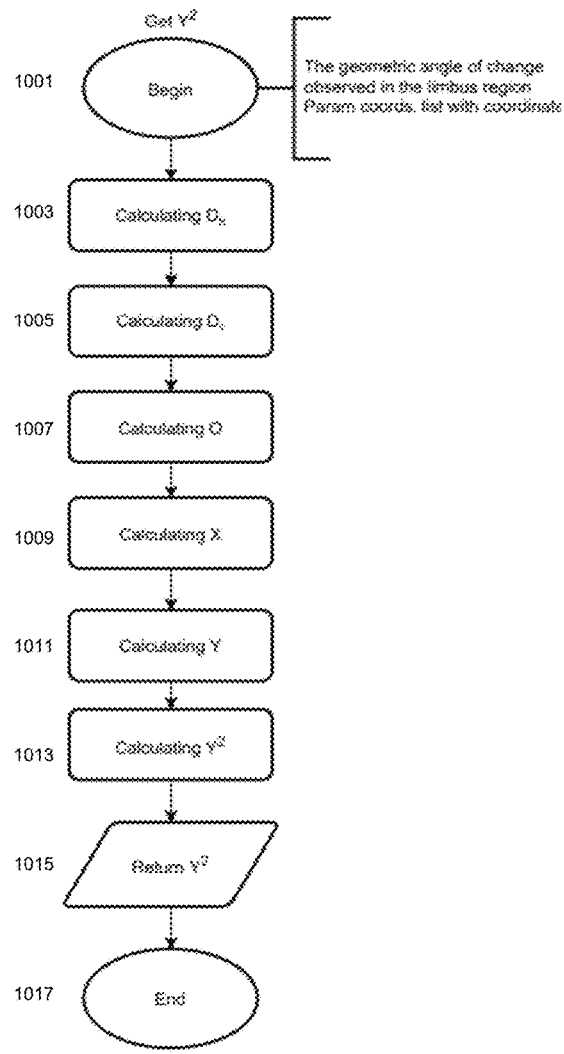
FIG. 10 is a flowchart describing the procedure for determining the geometric angle of change observed in the limbus region.

FIG. 10 shows a flowchart describing the process of an algorithm configured to determine the geometric angle of change observed in the limbus region. In step 1001, the algorithm may begin. In step 1003, the algorithm may calculate $D_h$. $D_h$ may be determined with the following expression: coords[0].get("w"). In step 1005, the algorithm may calculate $D_v$. $D_v$ may be determined with the following expression: coords[0].get("y"). In step 1007, the algorithm may calculate O. O may be determined with the following expression: $D_h/2$. In step 1009, the algorithm may calculate X. X may be determined with the following expression: coords[0].get("x"). In step 1011, the algorithm may calculate Y. Y may be determined with the following expression: coords[0].get("y"). In step 1013, the algorithm may calculate $Y^2$. $Y^2$ may be determined with the following expression: pow((pow($D_h$, 2)/4)−pow((Dh/Dv), 2)*pow(X, 2), 2). Steps 1003-1013 may incorporate the calculation of a value. The aforementioned values may be calculated with any variation on the aforementioned expressions or via similar expressions. In step 1015, the algorithm may return $Y^2$. The algorithm may end in step 1017.

Figure 11:
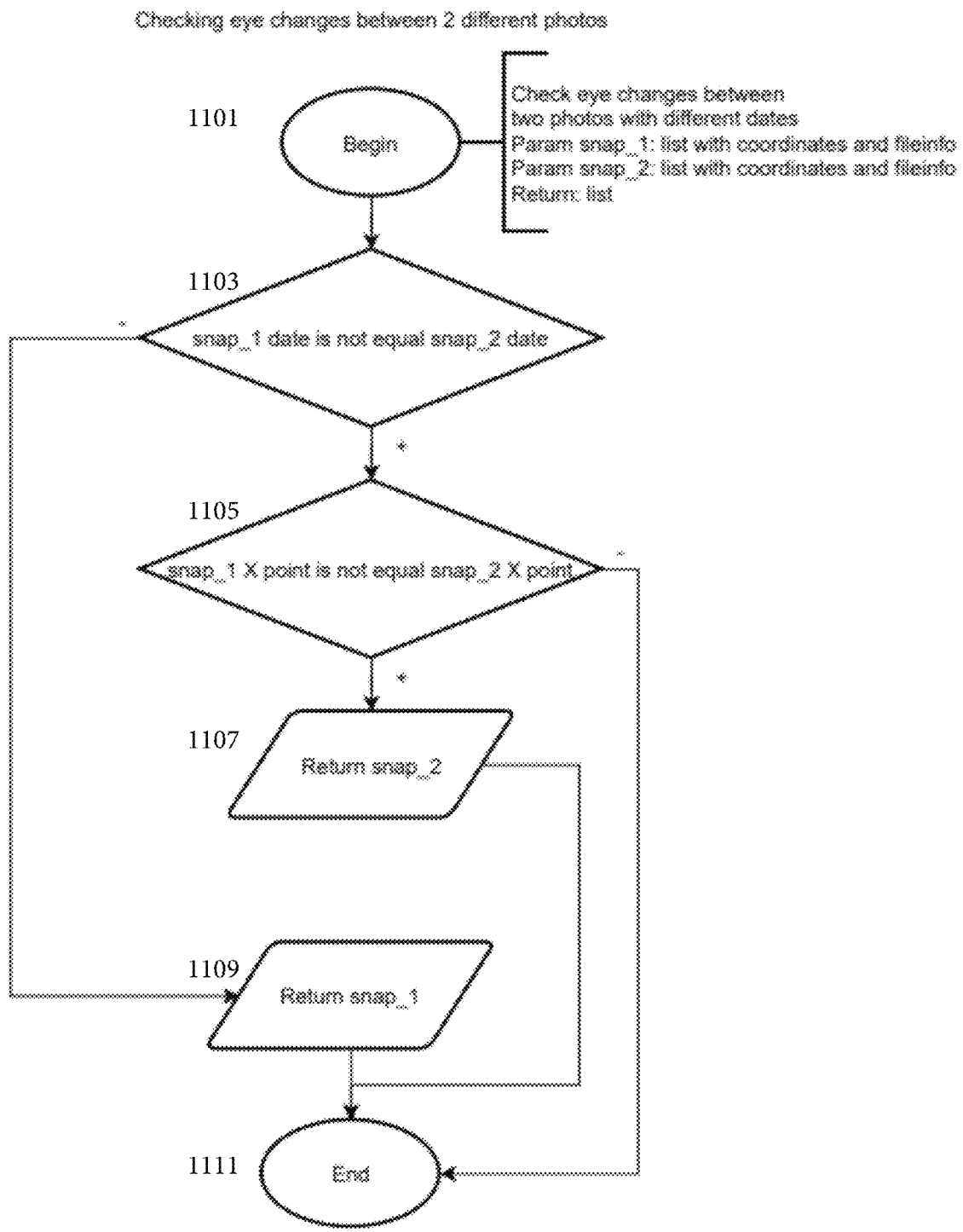
FIG. 11 is a flowchart describing the procedure for determining eye changes between two photos with different dates.

FIG. 11 shows a flowchart describing an algorithm process for determining eye changes between two photos with different dates. The algorithm may begin in step 1101. In step 1103, the algorithm may determine whether the snap_1 date is not equal to the snap_2 date. In this step, the algorithm may be deciphering whether two snapshots occurred on the same date. If snap_1 date is not equal to snap_2 date, then the algorithm continues to step 1105, where the algorithm determines whether snap_1 X point is not equal to snap_2 X point. If step 1105 returns yes (for example, when snap_1 X is not equal to snap_2 X), then the process continues to step 1107, where snap_2 is returned and the process ends at step 1111. If step 1105 returns no (for example, when snap_1 X is equal to snap), then the process continues to step 1107, which returns snap_2, and the process ends at step 1111. If in step 1103 the snap_1 date is equal to snap_2 date, then the process returns snap_1 in step 1109, and the process ends in step 1111.

Figure 12:
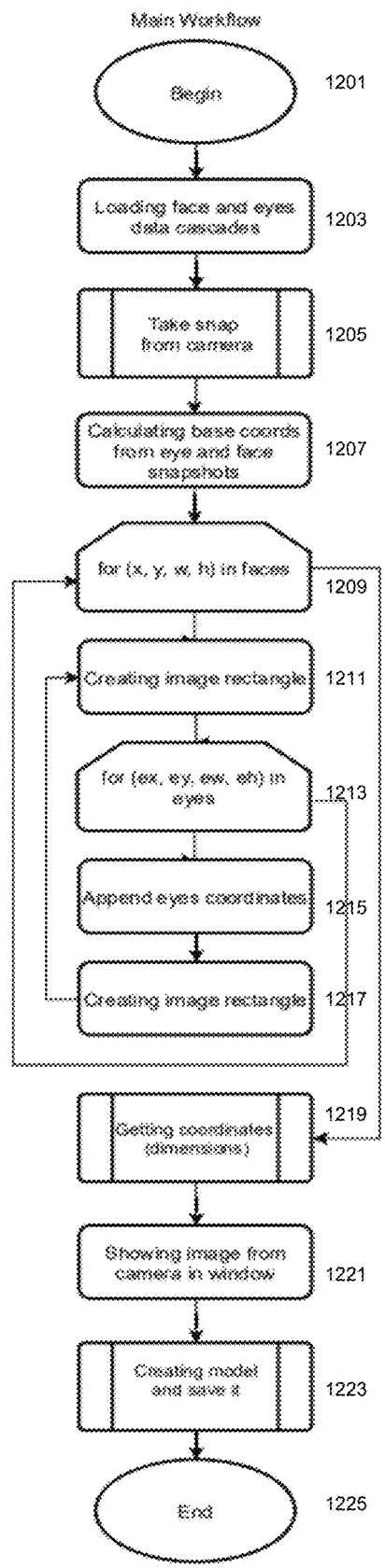
FIG. 12 is a flowchart describing the main workflow.

FIG. 12 shows a flowchart describing the main workflow. The main workflow may incorporate any of the aforementioned algorithms, variations of the aforementioned algorithms, or may incorporate algorithms not previously described. In step 1201, the algorithm may begin. In step 1203, the system may load face and eyes data cascades. In step 1205, the system may take a snapshot for the camera. Next, in step 1207, the system may calculate base coordinates from eye and face snapshots. The system may calculate base coordinates for (x, y, w, h) in faces, in step 1209. In step 1211, the system may create an image rectangle. Specifically, in step 1213, the system may do so for (ex, ey, ew, eh) in eyes. The system may then append eye coordinates in step 1215. Next, the system may then create an image rectangle (for example, based on coordinates of the eyes and face). In step 1219, the system may get coordinates (for example, dimensions). The dimensions may be a function of the eye coordinates. In step 1221, the system may show an image from the camera in a window. Next, in step 1223, the system may create a model and save it. The model may be a function expressed as: makeModel(dimensions, eyes_coord[0].get("w")). Finally, in step 1325, the workflow may end.

FIG. 13 shows an example of code that may be utilized for algorithms (for example, the aforementioned algorithms).

FIG. 14 shows an example of code that may be utilized to structure a database (for example, a database that may be utilized by the system).

While this invention has been described in conjunction with the embodiments outlined above, many alternatives, modifications and variations will be apparent to those skilled in the art upon reading the foregoing disclosure. Accordingly, the embodiments of the invention, as set forth above, are intended to be illustrative, not limiting. Various changes may be made without departing from the spirit and scope of the invention.

What is claimed is:

1. A system for measuring and assessing intra-ocular pressure (IOP), the system being carried out on an electronic device, the system comprising:
   a processor;
   a memory with a non-transitory computer readable storage medium;
   a camera; and
   computer-readable instructions written in the memory, wherein the instructions when executed by the processor cause the system to:
   capture one or more images of a user's eye;
   convert each of the one or more images to one or more three-dimensional images;
   analyze the one or more three-dimensional images; an
   calculate an IOP measurement.

2. The method of claim 1 further comprising the steps of:
   selecting a plurality of points on the user's eye;
   determining, for each of the plurality of points, a first camera origin coordinate
   and a second camera origin coordinate;
   determining, for each of the plurality of points, a first point projection and a second point projection; and
   determining, for each of the plurality of points, a camera distance,
      wherein the camera distance is distance between the first camera origin coordinate and the second camera origin coordinate.

3. The method of claim 2 further comprising the steps of:
   determining, for each of the plurality of points, a first retinal position and a second retinal position;
   calculating, for each of the plurality of points, a difference in retinal position,
      wherein the difference in retinal position is equal to the difference between the first retinal position and the second retinal position;
   calculating, for each of the plurality of points, a depth value,
      wherein the depth value is a function of the first camera origin coordinate, the second camera origin coordinate, the first point projection, and the second point projection, and
      wherein the depth value is proportional to a quotient of the camera distance and the difference in retinal position; and
   creating the one or more three-dimensional images based on the depth value for each of the plurality of points on the user's eye.

4. The method of claim 3 further comprising the steps of:
   determining, for each of the one or more three-dimensional images, a horizontal corneal diameter ($D_H$), a vertical corneal diameter ($D_V$), and a geometrical center of the corneal projection (O);
   determining, for each of the one or more three-dimensional images, X and Y based on a first camera origin coordinate and a second camera origin coordinate; and
   calculating $Y^2$ via:

$$Y^2 = \frac{D_H^2}{4} - \left(\frac{D_H}{D_V}\right)^2 \cdot X^2$$

wherein the IOP measurement is a function of $Y^2$.

5. The method of claim 4 further comprising the step of calibrating the camera.

6. The method of claim 5 wherein an eye zone is presented to the user when calibrating the camera.

7. The method of claim 5 further comprising the step of transmitting an alert to the user if the calibration is unsuccessful.

8. The system of claim 2 wherein the instruction to convert each of the one or more images to one or more three-dimensional images when executed by the processor causes the system to:
   select a plurality of points on the user's eye;
   determine, for each of the plurality of points, a first camera origin coordinate and a second camera origin coordinate;
   determine, for each of the plurality of points, a first point projection and a second point projection; and
   determine, for each of the plurality of points, a camera distance,
      wherein the camera distance is distance between the first camera origin coordinate and the second camera origin coordinate.

9. The system of claim 2 wherein the instruction to convert each of the one or more images to one or more three-dimensional images when executed by the processor further causes the system to:
   determine, for each of the plurality of points, a first retinal position and a second retinal position;
   calculate, for each of the plurality of points, a difference in retinal position,
      wherein the difference in retinal position is equal to the difference between the first retinal position and the second retinal position;
   calculate, for each of the plurality of points, a depth value,
      wherein the depth value is a function of the first camera origin coordinate, the second camera origin coordinate, the first point projection, and the second point projection, and
      wherein the depth value is proportional to a quotient of the camera distance and the difference in retinal position; and
   create the one or more three-dimensional images based on the depth value for each of the plurality of points on the user's eye.

10. The system of claim 9 wherein the instruction to calculate the IOP measurement when executed by the processor further causes the system to:
    determine, for each of the one or more three-dimensional images, a horizontal corneal diameter ($D_H$), a vertical corneal diameter ($D_V$), and a geometrical center of the corneal projection (O);
    determine, for each of the one or more three-dimensional images, X and Y based on a first camera origin coordinate and a second camera origin coordinate; and
    calculate $Y^2$ via:

$$Y^2 = \frac{D_H^2}{4} - \left(\frac{D_H}{D_V}\right)^2 \cdot X^2$$

wherein the IOP measurement is a function of $Y^2$.

11. The system of claim 1 wherein the instructions when executed by the processor cause the system to calibrate the camera.

12. The system of claim 11 further comprising an eye zone, wherein an eye zone is presented to the user during calibration of the camera.

13. The system of claim 11 wherein the instructions when executed by the processor cause the system to transmit an alert to the user if the calibration is unsuccessful.

14. The system of claim 1 wherein the instructions when executed by the processor cause the system to:
capture one or more subsequent images of the user's eye;
convert each of the one or more subsequent images to one or more three-dimensional subsequent images;
analyze the one or more subsequent three-dimensional images; and
calculate a subsequent IOP measurement.

15. The system of claim 14 wherein the instructions when executed by the processor cause the system to compare the IOP measurement and the subsequent IOP measurement, wherein the IOP measurement is a baseline IOP.

16. The system of claim 1 wherein the instructions when executed by the processor cause the system to alert the user if the subsequent IOP measurement differs from the baseline IOP by a pre-determined variance.

17. A method for measuring and assessing intra-ocular pressure (IOP) being carried out on an electronic device comprising a memory with a non-transitory computer readable storage medium, the method comprising the steps of:
capturing, via a camera, one or more images of a user's eye;
converting, via a processor, each of the one or more images to one or more three-dimensional images;
analyzing, via the processor, the one or more three-dimensional images; and
calculating, via the processor, an IOP measurement.

18. The method of claim 17 further comprising the steps of:
selecting a plurality of points on the user's eye;
determining, for each of the plurality of points, a first camera origin coordinate and a second camera origin coordinate;
determining, for each of the plurality of points, a first point projection and a second point projection; and
determining, for each of the plurality of points, a camera distance,
wherein the camera distance is distance between the first camera origin coordinate and the second camera origin coordinate.

19. The method of claim 18 further comprising the steps of:
determining, for each of the plurality of points, a first retinal position and a second retinal position;
calculating, for each of the plurality of points, a difference in retinal position,
wherein the difference in retinal position is equal to the difference between the first retinal position and the second retinal position;
calculating, for each of the plurality of points, a depth value,
wherein the depth value is a function of the first camera origin coordinate, the second camera origin coordinate, the first point projection, and the second point projection, and
wherein the depth value is proportional to a quotient of the camera distance and the difference in retinal position; and
creating the one or more three-dimensional images based on the depth value for each of the plurality of points on the user's eye.

20. The method of claim 19 further comprising the steps of:
determining, for each of the one or more three-dimensional images, a horizontal corneal diameter ($D_H$), a vertical corneal diameter ($D_V$), and a geometrical center of the corneal projection (O);
determining, for each of the one or more three-dimensional images, X and Y based on a first camera origin coordinate and a second camera origin coordinate; and
calculating $Y^2$ via:

$$Y^2 = \frac{D_H^2}{4} - \left(\frac{D_H}{D_V}\right)^2 \cdot X^2$$

wherein the IOP measurement is a function of $Y^2$.

21. The method of claim 17 further comprising the steps of:
capturing one or more subsequent images of the user's eye;
converting each of the one or more subsequent images to one or more three-dimensional subsequent images;
analyzing the one or more subsequent three-dimensional images; and
calculating a subsequent IOP measurement.

22. The method of claim 21 further comprising the step of comparing the IOP measurement and the subsequent IOP measurement, wherein the IOP measurement is a baseline IOP.

23. The method of claim 17 further comprising the step of alerting the user if the subsequent IOP measurement differs from the baseline IOP by a pre-determined variance.

24. The method of claim 21 further comprising the steps of:
determining whether the one or more images and the one or more subsequent images were captured on a same date;
preparing a first list of coordinates and a second list of coordinates,
wherein the first list of coordinates contain coordinates of the user's eye as represented in the one or more images and the second list of coordinates contain coordinates of the user's eye as represented in the one or more subsequent images;
determining whether the first list of coordinates and the second list of coordinates contain the same coordinates; and
returning the second list of coordinates if the first list of coordinates and the second list of coordinates are unequal.

* * * * *